United States Patent [19]
Hurlbert

[11] Patent Number: 6,146,382
[45] Date of Patent: Nov. 14, 2000

[54] OCCIPITO-CERVICAL STABILIZATION SYSTEM AND METHOD

[75] Inventor: R. John Hurlbert, Calgary, Canada

[73] Assignee: Spinal Concepts, Inc., Austin, Tex.

[21] Appl. No.: 09/159,303

[22] Filed: Sep. 23, 1998

[51] Int. Cl.[7] .................................................. A61B 17/56
[52] U.S. Cl. ............................................................. 606/61
[58] Field of Search .................................. 606/61, 60, 62, 606/69, 64, 70, 71

[56] References Cited

U.S. PATENT DOCUMENTS

| | | |
|---|---|---|
| 4,763,644 | 8/1988 | Webb . |
| 4,805,602 | 2/1989 | Puno et al. . |
| 4,841,959 | 1/1991 | Ransford .................................. 606/61 |
| 4,887,596 | 12/1989 | Sherman . |
| 4,950,269 | 8/1990 | Gaines, Jr. . |
| 4,987,892 | 1/1991 | Krag et al. ................................ 606/61 |
| 5,129,388 | 7/1992 | Vignaud et al. . |
| 5,360,429 | 11/1994 | Jeason et al. ............................. 606/61 |
| 5,545,164 | 8/1996 | Howland ................................... 606/61 |
| 5,662,651 | 9/1997 | Tornier et al. ............................ 606/61 |

OTHER PUBLICATIONS

"Olerud Cervical TM," NordOpedic AB, 1996.
Carlson et al., "Surgical Techniques for Occiput to C2 Arthrodesis," Posterior Cervical Spine Surgery, Principles and Techniques in Spine Surgery, Lippincott–Raven 1998, pp. 41–52.

"Posterior cervical and occipito–cervical spine fixation system," Biomat, Oct. 1997.

*Primary Examiner*—Michael Buiz
*Assistant Examiner*—Tan-Uyen T. Ho
*Attorney, Agent, or Firm*—Conley, Rose & Tayon, PC; Eric B. Meyertons

[57] ABSTRACT

A spinal fixation system and method for mechanically fusing a skull and a portion of a spine are described. In an embodiment, the fixation system includes a plate, connecting members for attaching the plate to a skull, and a cable assembly configured to form an engagement between the plate and the spine. In an embodiment, the fixation system may further include bone graft material placed between the skull and one or more vertebrae. In an alternative embodiment, the spinal fixation system may include a plate with an attached pair of arms. The arms may be permanently attached to the plate. Alternatively, the arms may be reversibly attached to the plate. The fixation system preferably includes connecting members for connecting the plate to the skull. The fixation system preferably further includes an anchoring system for connecting the fixation system to at least one vertebra of the spine. The anchoring system may include anchoring bolts attached to the arms by connectors. In an embodiment, the fixation system further includes a cable assembly configured to form an engagement between the plate and the spine. In a further embodiment, the fixation system may further include bone graft material placed between the skull and one or more vertebrae of the spine and a cable assembly to hold the bone graft material in compression.

34 Claims, 9 Drawing Sheets

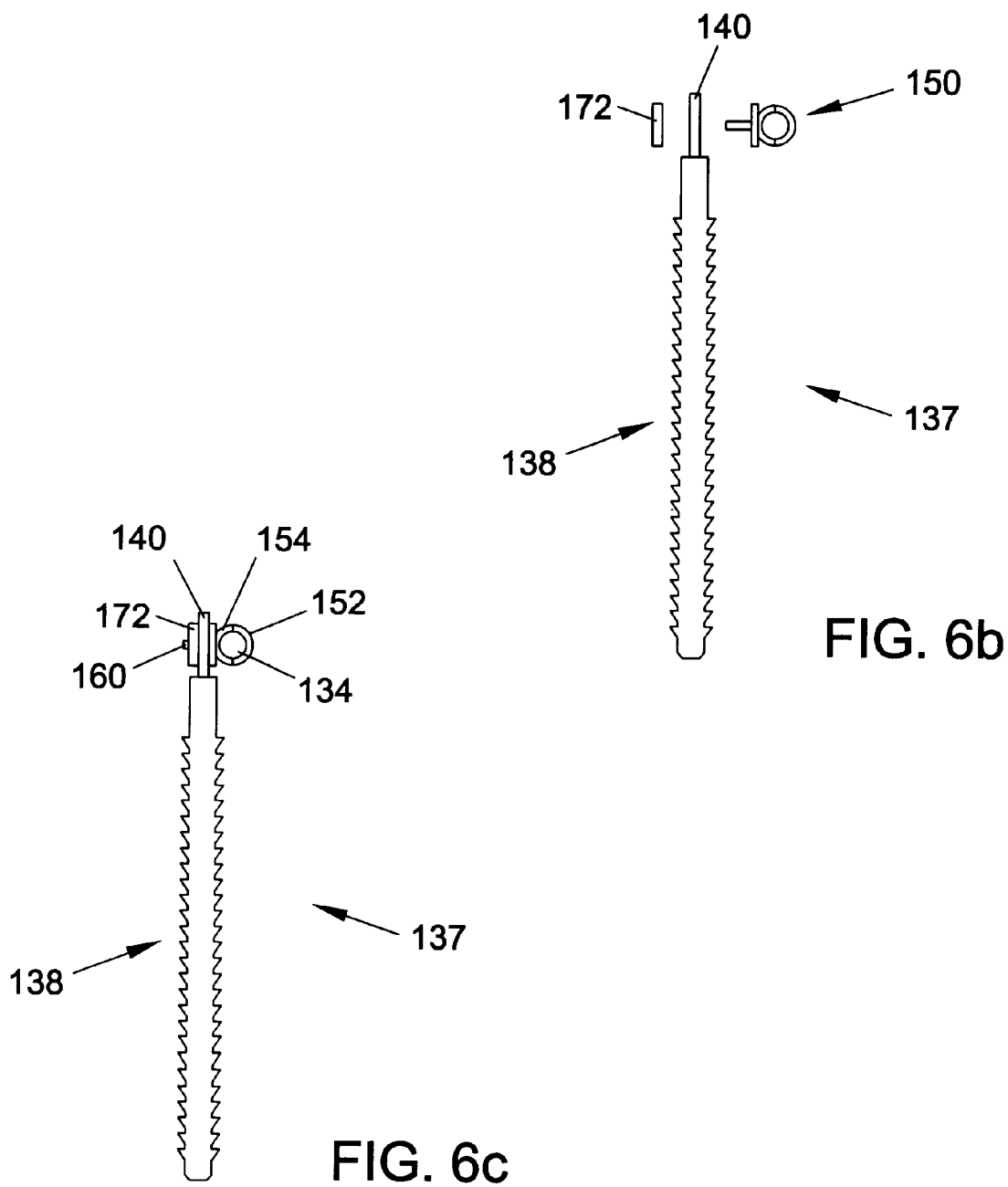

OCCIPITO-CERVICAL STABILIZATION SYSTEM AND METHOD

BACKGROUND OF THE INVENTION

1. Field of the Invention

The present invention generally relates to spinal fixation systems and the like. More particularly, an embodiment of the invention relates to a spinal implant system for correction, fixation, and stabilization of a human spine to allow the development of a solid spinal fusion.

2. Description of the Related Art

Spinal fixation, such as lumbar sacral fusion and the correction of spinal deformities such as scoliotic curves, is a well known and frequently used medical procedure. Pedicle, lateral, and oblique mounting devices may be used to secure corrective spinal instrumentation to a portion of the spine that has been selected to be fused by arthrodesis.

A spinal fixation system typically includes corrective spinal instrumentation that is attached to selected vertebrae of the spine by screws, hooks, and clamps. The corrective spinal instrumentation includes spinal rods or plates that are generally parallel to the patient's back. The corrective spinal instrumentation may also include transverse connecting rods that extend between neighboring spinal rods. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of a patient's spine. Examples of pedicle screws and other types of attachments are illustrated in U.S. Pat. Nos. 4,763,644; 4,805,602; 4,887,596; 4,950,269; and 5,129,388. Each of these patents is incorporated by reference as if fully set forth herein.

Fixation of the skull to the cervical spine may be used to treat trauma to the neck, degenerative diseases such as rheumatoid arthritis, and pain that is otherwise unresponsive to treatment. Current implantable devices designed to immobilize the skull with respect to the upper cervical spine have to be individually tailored. Often, such devices are assemblies of several components not designed specifically for fusing the cervical spine to the skull.

SUMMARY OF THE INVENTION

An embodiment of the invention relates to a stabilization system designed to mechanically fixate a human skull to an upper cervical portion of a human spine. The stabilization system may include a plate having one or more arms coupled thereto, anchoring bolts configured to engage the spine, connecting members configured to secure the plate to the skull, and connectors adapted to join the arms to the anchoring bolts. The members of the stabilization system are preferably formed of a biocompatible material. For purposes of this description, "biocompatible material" is material not rejected by the body and/or not causing infection or allergic reaction following implantation. Examples of biocompatible material include titanium or stainless steel.

The plate preferably is contoured to maximize contact between the plate and the skull. The plate preferably includes a plurality of holes through which the connecting members pass to secure the plate to the skull. The connecting members may include upper portions and lower portions having a diameter less than a diameter of the upper portions. The connecting members may be configured such that, when the plate is secured to the skull, upper surfaces of the connecting member are substantially coplanar with an upper surface of the plate. In a preferred embodiment, the connecting members are bone screws.

The plate and the arms may be formed as a single unit. Alternatively, the arms may be fabricated separately from the plate and subsequently coupled to the plate either permanently (e.g., by welding or soldering) or reversibly (e.g., by screwing). The arms may be textured so as to inhibit movement of the arms with respect to the spine when the system is in use. In preferred embodiments the arms are configured to align along opposite sides of a spine. This configuration may be accomplished by the use of two arms disposed on opposite sides of the plate, or a single arm may be attached to the plate such that the arm bifurcates to align a member along each side of a spine, for example.

Preferably, each of the arms includes a portion proximate the plate and a portion distal to the plate. The proximate portion is preferably oriented at an angle to the distal portion such that a natural curvature of the spine may be maintained upon fusion of the spine. The angle may be in the range of about from 100° to about 140°, a preferred angle in certain embodiments is approximately 120°.

The anchoring bolts are inserted into at least one vertebra of the spine so as to facilitate fusion of the skull to the upper cervical portion of the spine. In an embodiment the anchoring bolts may be inserted into holes formed in the at least one vertebra. In an embodiment, the anchoring bolts span the transarticular joint space between cervical vertebrae C1 and C2. The anchoring bolts may be cannulated to facilitate use of a K-wire or guidewire for guiding the anchoring bolts into place. In an embodiment, each of the anchoring bolts may include a substantially smooth, unthreaded shank. In an alternative embodiment, each of the anchoring bolts may include a shank comprising a threaded portion and/or a tap relief for self-tapping.

Each of the connectors may include two pieces. A threaded projection may extend from the first piece. The threaded projection may be configured to pass through a hole defined by the second piece. Each of the anchoring bolts may further include a belt head. The bolt head may define holes through which the projections may pass. A surface of each of the bolt heads and a surface of each of the connectors may define radially oriented serrations. The serrations may serve to effect engagement between the bolt heads and the connectors so as to inhibit rotation of the anchoring bolts with respect to the arms. The system may further include locking nuts that are screwed onto the threaded projections to secure the anchoring bolts to the arms. Preferably, the anchoring bolts are oriented at an angle of approximately 65° with respect to the arms during use to maintain a substantially natural curvature of the spine.

In an alternative embodiment, the system may include a cable assembly. The cable assembly may be attached to the plate through, e.g., slots or fasteners. In an embodiment, the system may further include bone graft material inserted between the skull and one of the vertebrae, along with a cable assembly. The cable assembly may include two cables; or, the cable assembly may include a single cable. The cables are preferably flexible such that they may form a loop engaging the spinous process of the vertebra. Each of the cables may have a hook affixed at one end for engaging slots in the plate. In an embodiment, the first cable may have a mechanism affixed to an end opposite the hook for connecting the first cable to the second cable. In an alternative embodiment, the connecting mechanism may be separate from either of the cables. In an embodiment, the connecting mechanism may be a crimp. The cable assembly may be configured to pass around the spinous process of the vertebra and engage the slots in the plate, such that the bone graft material is compressed between the skull and the vertebra. The bone graft material may serve to further facilitate fusion between the skull and the upper cervical spine.

In yet another alternative embodiment, the system may include a plate, connecting members to secure the plate to the skull, and a cable assembly. The plate preferably is contoured to maximize contact between the plate and the skull. The plate preferably defines a plurality of holes through which the connecting members pass to secure the plate to the skull. The cable assembly may include a pair of cables; alternatively, the cable assembly may include a single cable. The cables are preferably attached to the plate via, e.g., slots or fasteners. In a preferred embodiment, the plate includes slots into which the ends of the cables are inserted. The connecting members may include upper portions and lower portions having a diameter less than the diameter of the upper portions. The connecting members may be configured such that, when the plate is secured to the skull, upper surfaces of each of the connecting members are substantially coplanar with an upper surface of the plate. In a preferred embodiment, the connecting members are screws.

The cable assembly may include two cables. Each of the cables may have a hook affixed at one end. In an embodiment, the first cable may have a mechanism affixed to an end opposite the hook for connecting the first cable to the second cable. In an alternative embodiment, the connecting mechanism may be separate from either of the cables. In an embodiment, the connecting mechanism may be a crimp. The cable assembly may be configured to pass around the spinous process of the vertebra and engage the slots in the plate. In an embodiment, the system may further include bone graft material placed between the skull and at least one of the vertebrae. The cable assembly may form an engagement between the skull and the vertebra such that the bone graft material is compressed between the skull and the vertebra. The bone graft material may serve to further facilitate fusion between the skull and the upper cervical spine.

With respect to assembly and implantation of the stabilization system, in an embodiment, a surgeon prepares at least one vertebral junction for receiving the anchoring bolts. This preparation usually involves using a K-wire or guidewire to guide the anchoring bolts into place. The anchoring bolts may be inserted into holes formed in the vertebra or vertebrae. Alternatively, the anchoring bolts may be screwed into at least one of the vertebrae such that the anchoring bolts form openings as they are screwed in. The surgeon may further prepare the skull for receiving the connecting members by forming a plurality of holes in the occiput of the skull aligned with the holes in the plate. The connecting members may then be inserted through the holes in the plate and the holes in the skull to secure the plate to the skull. First and second connector pieces may then be affixed to the arms. The projection of the first connector piece may be inserted through the hole in the head of the anchoring bolt and secured to the anchoring bolt by a locking nut.

In an alternative embodiment, a cable assembly may be affixed to the stabilization system. First and second cables may be attached to the stabilization system and positioned around the spinous process of a vertebra. The cables may be tightened to apply a compressive force to the vertebrae of the spine and further promote spinal fusion. The tightened cables may then be secured to one another by attaching to the second cable a connecting mechanism affixed to an end of the first cable. Alternatively, the tightened cables may be secured by attaching to both cables a connecting mechanism. Optionally, bone graft material may be packed between the skull and at least one of the vertebrae of the spine prior to placement and tightening of the cables.

In yet another embodiment, a stabilization system may be attached to a skull and a portion of a spine by forming a plurality of holes in the occiput of the skull aligned with holes in a plate. The connecting members may then be inserted through the holes in the plate and the holes in the skull to secure the plate to the skull. First and second cables may be attached to the stabilization system and positioned around the spinous process of a vertebra. The cables may be tightened to apply a compressive force to the vertebrae of the spine and further promote spinal fusion. The tightened cables may then be secured to one another by attaching to the second cable a connecting mechanism affixed to an end of the first cable. Alternatively, the tightened cables may be secured by attaching to both cables a connecting mechanism. Optionally, bone graft material may be packed between the skull and at least one of the vertebrae of the spine prior to placement and tightening of the cables.

Disclosed herein are also methods of manufacturing a spinal fixation system comprising providing a plate configured for attachment to an occiput, wherein the plate contains holes configured to accept bone screws, and wherein one or more arms are affixed to the plate for engaging a cervical vertebra; providing anchor bolts for attachment to one or more vertebrae; and providing connectors for securing the one or more arms to the anchor bolts. The method may be further described as comprising providing bone screws for attaching the plate to an occiput, and as further comprising providing a cable assembly for engaging a spinous process, wherein the cable assembly comprises hooks for attachment to the plate, and further providing slots in the plate to receive the hooks.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 5b depicts a front view of the components of the connector of FIG. 5a;

FIG. 6a depicts a front view of a locking nut;

FIG. 6b depicts an exploded side view of the components of an anchoring system;

FIG. 6c depicts a side view of the anchoring system of FIG. 6b in an assembled configuration;

Figure 1:
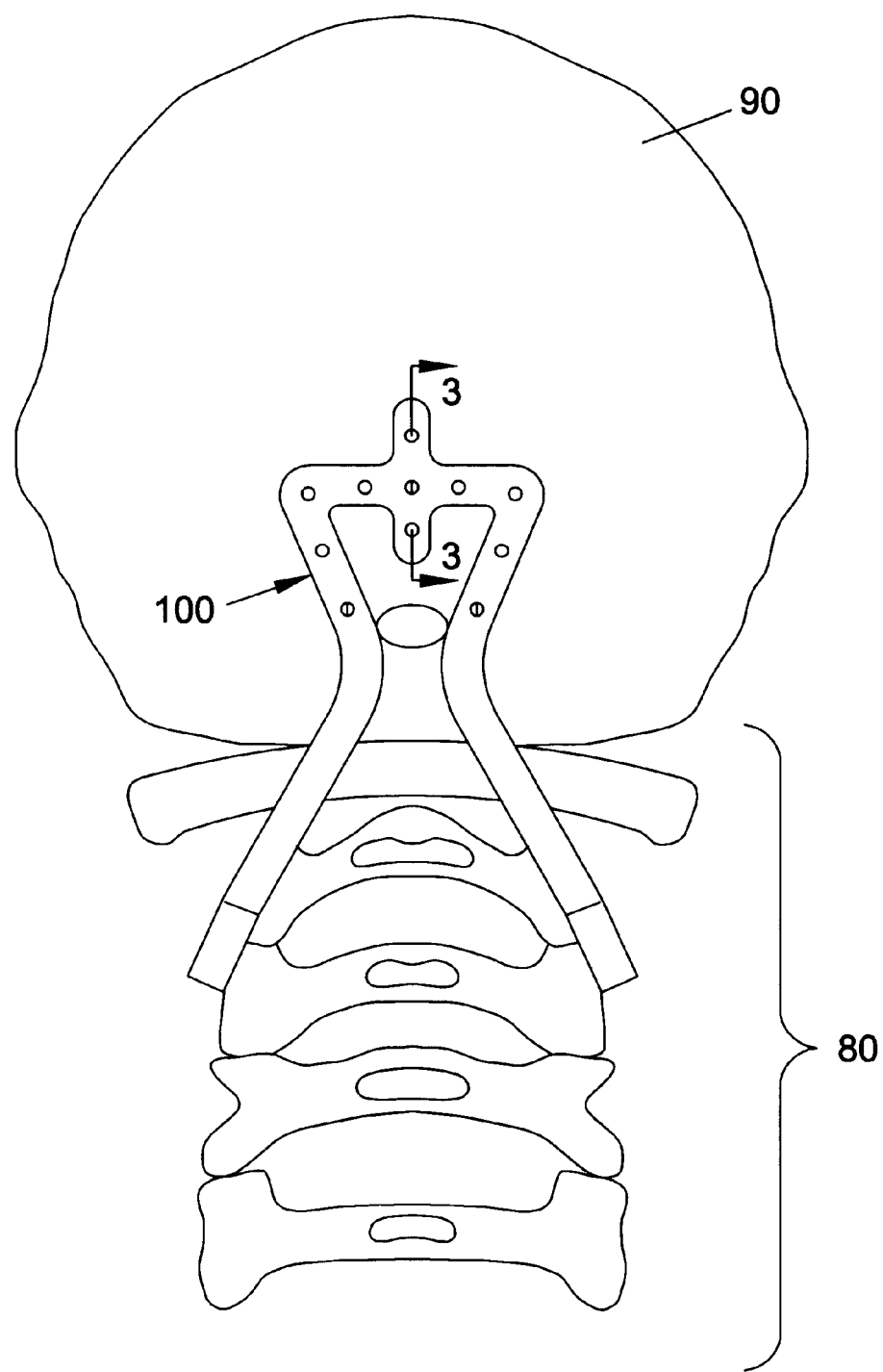
FIG. 1 depicts an embodiment of an occipito-cervical spinal fixation system in use.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE PREFERRED EMBODIMENTS

Figure 2A:
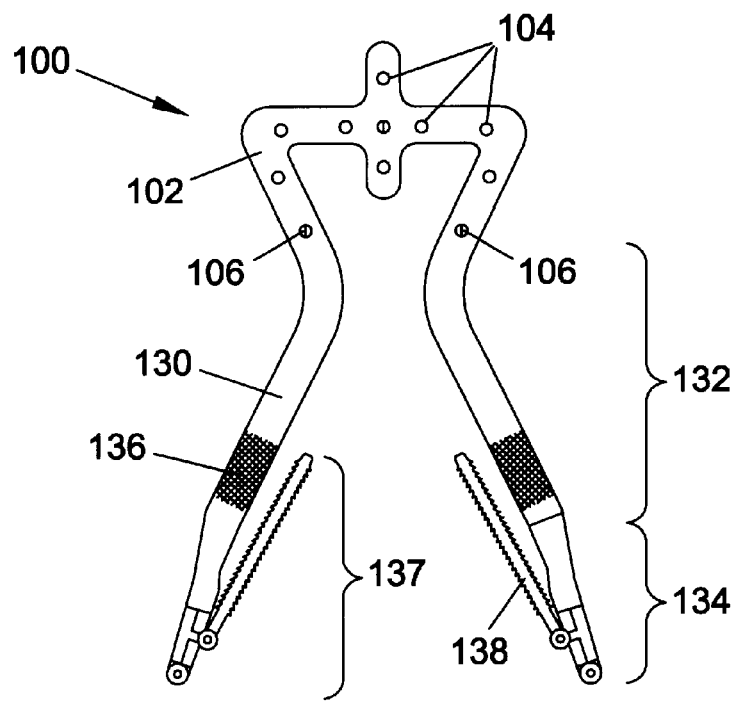
FIGS. 2a and 2b depict the fixation system of FIG. 1 in isolation.

Referring to FIG. 1, an embodiment of an occipito-cervical spinal fixation system is depicted in use. FIG. 1 depicts spinal fixation system 100 viewed looking upward along a portion of spinal column 80 toward occiput 90 of a skull. Turning now to FIG. 2a, spinal fixation system 100 is depicted in isolation from the same perspective used in FIG. 1. In an embodiment, spinal fixation system 100 includes arms 130 coupled to plate 102. Plate 102 and arms 130 are preferably configured to substantially immobilize the skull with respect to the spinal column during use. Plate 102 and arms 130 may be formed as a single piece. Alternatively, arms 130 may be formed separately from plate 102 and fixedly attached to plate 102 by, e.g., welding or soldering. In still another alternative embodiment, arms 130 may be formed separately from plate 102 and reversibly attached to plate 102 by coupling devices such as screws, or by a threaded connection. The fixation system is preferably made from a biocompatible material such as titanium or stainless steel.

Figure 3:
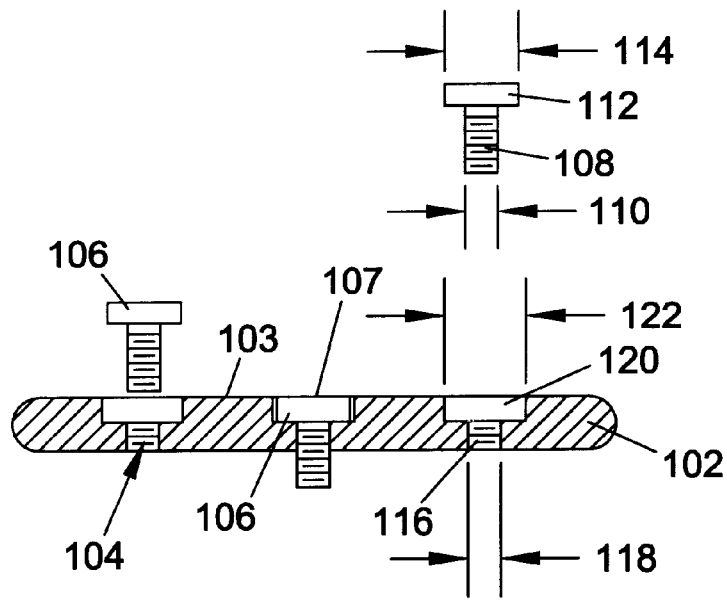
FIG. 3 depicts a cross-sectional view of connecting members and a plate portion of the fixation system of FIG. 1.

Plate 102 preferably includes a plurality of openings 104 formed therein for receiving connecting members 106. During use, connecting members 106 may be inserted into holes formed in the skull to secure the plate to the occiput such that movement of the skull with respect to a portion of the spine is inhibited. Connecting members 106 are preferably configured such that a diameter of an upper portion of each of the connecting members is greater than a diameter of openings 102. FIG. 3 depicts a cross-sectional view of an embodiment of connecting members 106 and plate 102. Connecting members 106 preferably include lower portion 108 having a diameter 110 and upper portion 112 having a diameter 114 greater than diameter 110. As depicted, diameters 110 and 114 are substantially constant. Alternatively, diameter 114 of upper portion 112 may increase with increasing distance from lower portion 108. Preferably, plate 102 is contoured to maximize contact with occiput 90 during use (FIG. 1).

Openings 104 in plate 102 preferably include first portion 116 having a diameter 118 and second portion 120 having a diameter 122 greater than diameter 118. Diameter 118 is preferably less than diameter 114 such that connecting member 106 may not pass completely through opening 104. As such, connecting members 106 preferably form a fixable engagement with plate 102 during use, to secure the plate to a portion of a skull. In an embodiment, both connecting member 106 and opening 104 include complementary threading on at least lower portion 108 and first portion 116, respectively. In a preferred embodiment, upper surface 107 of connecting member 106 is substantially coplanar with upper surface 103 of plate 102 during use.

Figure 2B:
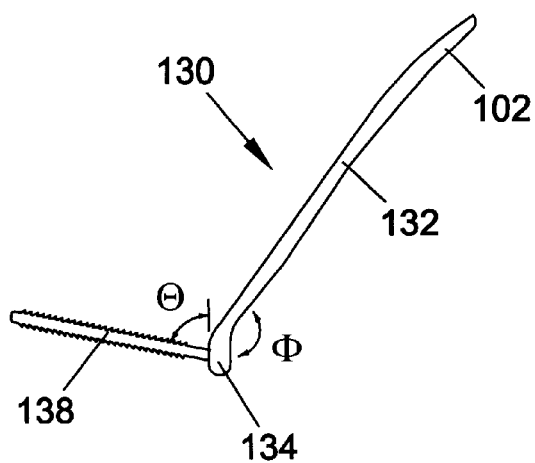

Turning to FIG. 2b, arms 130 preferably include proximate portion 132 adjacent plate 102 and distal portion 134 adjacent proximate portion 132. Preferably, the distal portions are oriented at an angle Φ to the proximate portions such that a substantially natural curvature of the spine may be maintained upon fusion of the spine. Preferably, the angle Φ is between about 100° and about 150°, depending on patient morphology. In an embodiment, arms 130 may include textured regions such as regions 136 shown in FIG. 2a. Textured regions 136 may include, for example, protrusions extending from the surface of the arms or pattered grooves formed within the surface of the arms. The textured regions may form an engagement with one or more vertebrae of spine 80 and/or occiput 90 during use to inhibit movement of the arms with respect to the spine and skull (FIG. 1).

Figure 4:
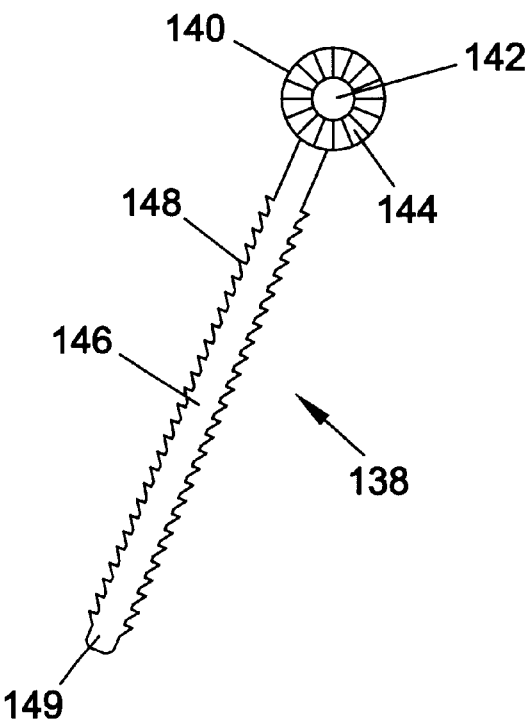
FIG. 4 depicts a front view of an anchoring bolt of the fixation system of FIG. 1.

Fixation system 100 preferably further includes anchoring system 137. In an embodiment, anchoring system 137 includes anchoring bolts 138 for engaging at least one vertebra of spinal column 80 (FIG. 2a). A front view of an anchoring bolt 138 is depicted in FIG. 4. Anchoring bolt 138 preferably includes bolt head 140 with opening 142 formed therethrough. Bolt head 140 preferably includes radially oriented serrations 144 on at least one surface of the bolt head. Anchoring bolt 138 further includes shank 146. In an embodiment, outer surface 148 of shank 146 includes threading. The threading may facilitate formation of an engagement between the anchoring bolt and at least one vertebra of spine 80 during use. Shank 146 may include tap relief 149. Alternatively, shank 146 may be substantially unthreaded. In an embodiment, anchoring bolts 138 may include a cannula extending longitudinally through the anchoring bolt.

During use, anchoring bolts 138 are preferably attached to distal portions 134 of arms 130 by connectors. In an embodiment depicted in FIGS. 5a (perspective view) and 5b (front view), connectors 150 include first piece 152 and second piece 154. First piece 152 preferably includes curved portion 156 and annular portion 158. Annular portion 158 preferably includes projection 160; in an embodiment, outer surface 162 of projection 160 includes threading. Second piece 154 preferably includes support portion 164 and curved portions 166. Opening 168 is preferably formed in support portion 164. FIG. 5c shows first piece 152 and second piece 154 in an engaged configuration. During, use, a surgeon may insert projection 160 into opening 168. Projection 160 preferably extends beyond an outer surface of support portion 164 of second piece 154 during use. When in the engaged configuration, curved portions 156 and 166, and annular portion 164 preferably form a channel 170.

Turning now to FIG. 6a, locking nut 172 is depicted in front view. Locking nut 172 preferably includes hole 174 therethrough. Preferably, an inner surface of hole 174 includes threading complementary to the threading of projection 160 of first piece 152. In an embodiment, outer surface 176 of locking nut 172 includes radially oriented serrations 178 similar to serrations 144 of bolt head 140.

FIG. 6b depicts an exploded side view of the components of anchoring system 137, and FIG. 6c depicts a side view of anchoring system 137 in an assembled configuration.

Figure 5A:
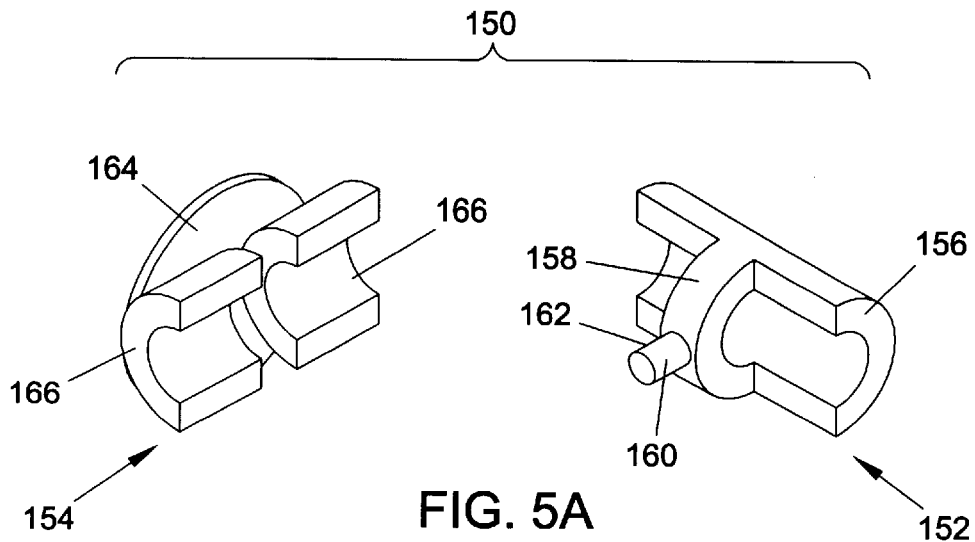
FIG. 5a depicts a perspective view of components of a connector used to attach an anchoring bolt to an arm of the fixation system of FIG. 1.
Figure 5B:
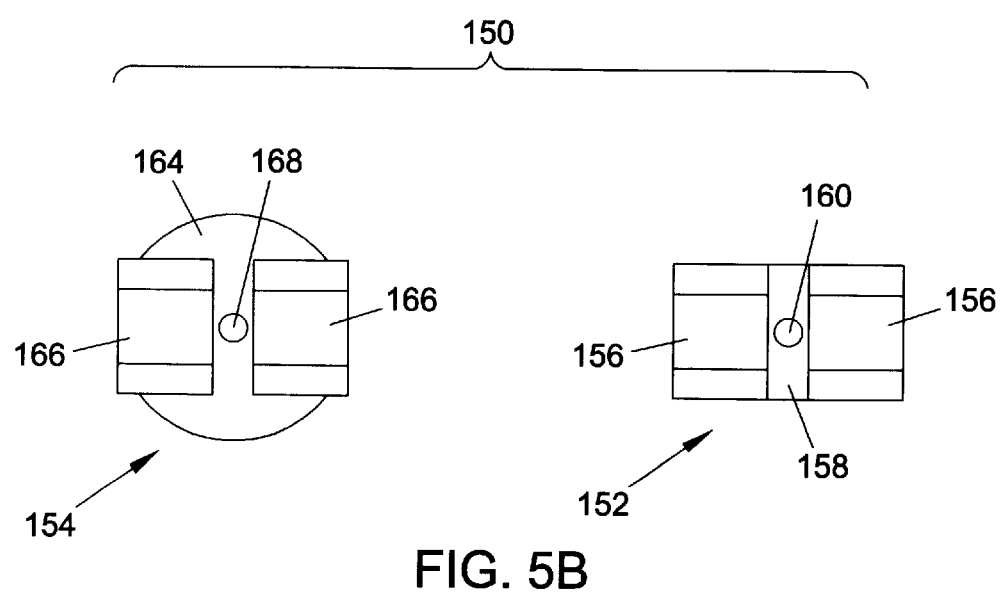
Figure 5C:
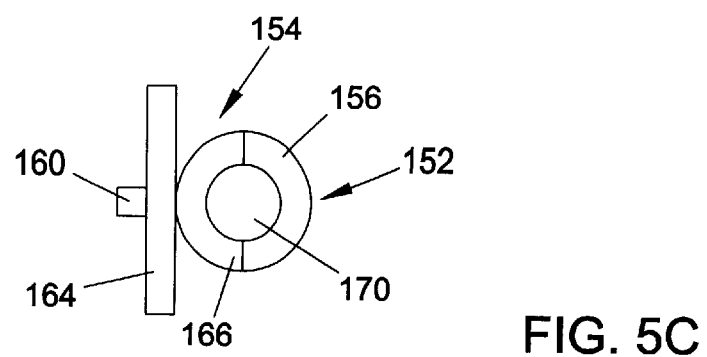
FIG. 5c depicts the connector of FIG. 5a in an engaged configuration.

Referring to FIG. 6c, a surgeon may insert distal portion 134 of arm 130 (FIG. 2a) through annular portion 158 of first piece 152 (FIG. 5a). Projection 160 of first piece 152 may then be inserted through opening 168 of second piece 154 (FIG. 5b) such that distal portion 134 of arm 130 is surrounded by the assembled connector. Projection 160 may then be inserted through opening 142 of bolt head 140 (FIG. 4). Locking nut 172 (FIG. 6a) may be attached to projection 160 such that a fixable engagement is thus formed between projection 160 and locking nut 172 to secure anchoring bolt 138 to connector 150, and thus to arm 130. As a result, arm 130 may be secured to connector 150 such that motion of the arm within the connector is substantially inhibited. Serrations 144 on bolt head 140 (FIG. 4) and serrations 178 on locking nut 172 (FIG. 6a) preferably form a fixable engagement between anchoring bolt 138 and locking nut 172 to prevent rotation of anchoring bolt 138 about projection 160 and to maintain the engagement between arms 130 and anchoring bolts 138.

Figure 7:
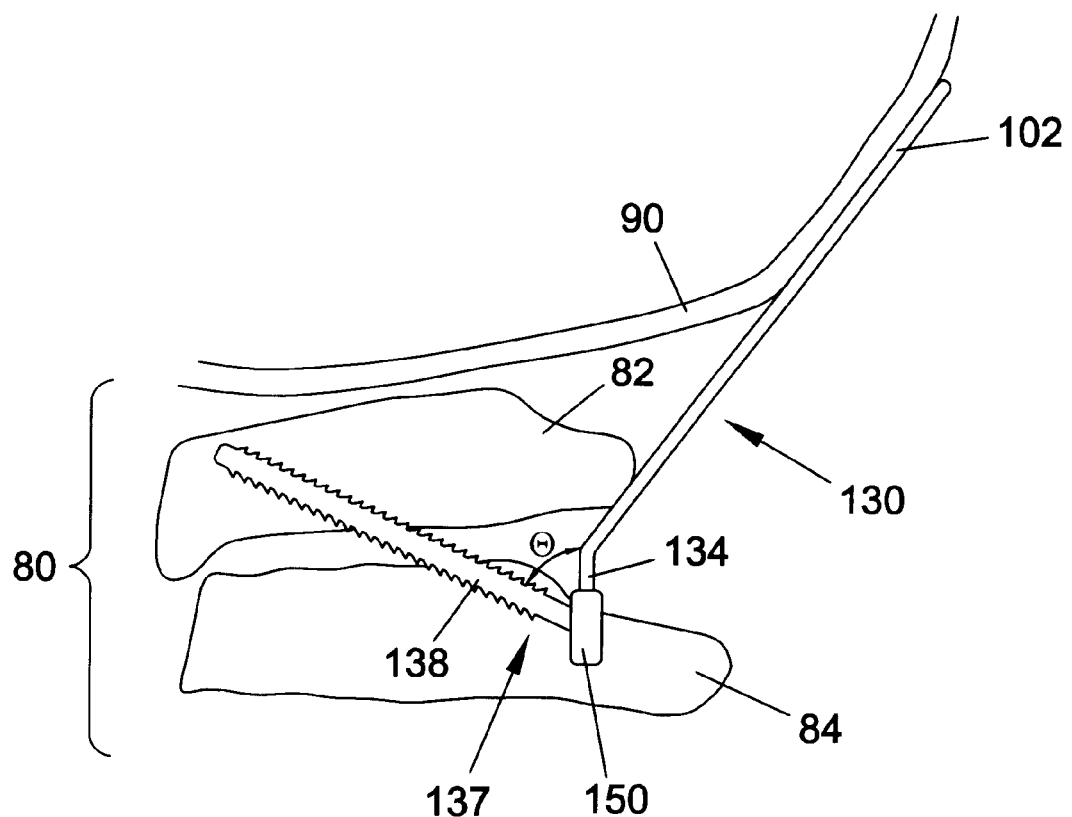
FIG. 7 depicts a side cross-sectional side view of the fixation system of FIG. 1 in use.

Turning now to FIG. 7, a side view of occipito-cervical spinal fixation system 100 in use is illustrated in cross-section. As depicted, a fixable engagement has been formed between plate 102 and occiput 90. To form the fixable engagement, a surgeon may form a plurality of holes within skull 90 and affix the plate to the skull by inserting connectors through holes in the plate and the holes in the skull. The surgeon may further form a fixable engagement between anchoring bolts 138 and spinal column 80 by inserting transarticular anchoring bolts between cervical vertebrae C1 and C2. Anchoring bolts or screws may be inserted between additional vertebral segments instead of, or in addition to, the C1/C2 transarticular space as the surgeon sees fit. Alternatively, the anchoring bolts may be driven into one or more vertebra by means of a tap relief on the anchoring bolts, such that the anchoring bolts form their own holes as they are inserted into the spine. As depicted in FIG. 7, anchoring bolts 138 form an engagement with spinal column 80 through vertebra 84. If vertebra 84 is second cervical vertebra C2, anchoring system 137 may be configured such that the engagement is formed with the pars interarticularis of cervical vertebra C2 connecting through to cervical vertebra C1. In an alternative embodiment, anchoring bolts 138 may form an engagement with cervical vertebrae 82 and 84. If vertebrae 82 and 84 are cervical vertebrae C1 and C2, respectively, anchoring system 137 may be configured such that anchoring bolt 138 spans a lateral joint space between the vertebrae.

Anchoring bolts 138 are oriented at an angle Θ with respect to distal portion 134 of arm 130. Angle Θ may be varied, depending on the anatomy of the patient. Preferably, angle Θ varies between about 55° and about 75°, based on the patient's morphology (FIG. 7). As described previously for FIG. 6c, anchoring system 137 may be attached to arms 130 by connector 150 such that skull 90 is substantially immobilized with respect to a portion of spinal column 80, thus promoting fusion between the skull and the portion of the spine.

In an alternate embodiment, the spinal fixation system may include a cable assembly attached to the plate or the arms. In an embodiment, hooks or other connectors attached to a cable may engage the plate through slots or other openings formed in the plate. Alternatively, the cable may be passed through a hole or other opening formed in the plate and secured with a crimp or other fastener. The fastener may be a part of the plate or separate from the plate. In an embodiment, one end of the cable may include a ball having a diameter larger than a diameter of the opening such that the cable may not be pulled completely through the opening.

Figure 8:
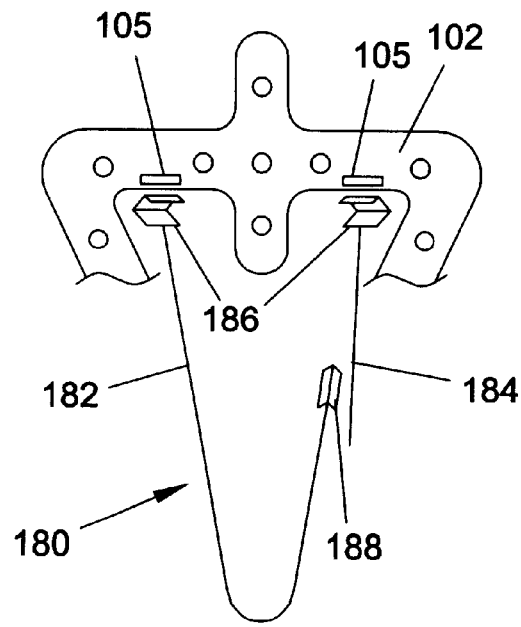
FIG. 8 depicts an alternative embodiment of a plate portion of the fixation system of FIG. 1.

As depicted in FIG. 8, plate 102 may further include slots 105. Spinal fixation system 100 may further include cable assembly 180. Cable assembly 180 may include first cable 182 and second cable 184. Alternatively, the cable assembly may include a single cable. The term "cable" within the context of this application means any elongated flexible member, including single-strand elements (e.g., stainless steel wires, monofilament lines, etc.) and multi-strand elements (cords, threads, twisted wires bundled together, etc.). Cables 182 and 184 may include any substantially flexible material including, but not limited to, cloth, fiber, steel, nylon, monofilament, or various plastics. The cables are preferably made of a biocompatible material such as titanium or stainless steel.

Figure 9:
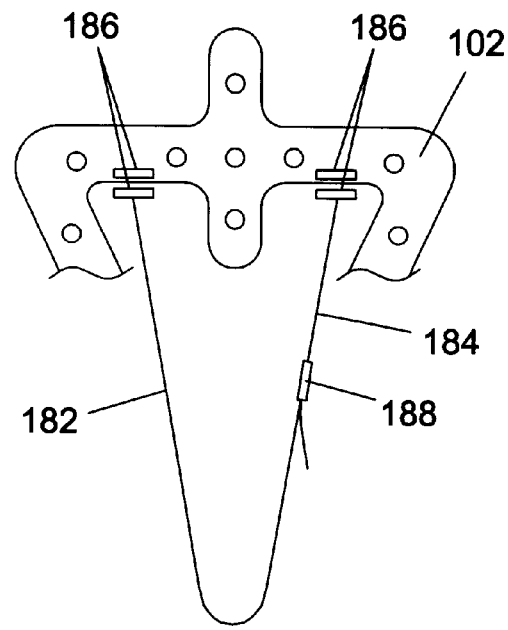
FIG. 9 depicts the spinal fixation system of FIG. 8 in an assembled configuration.

In an embodiment, hooks 186 may be attached to one of the ends of each of the cables. As depicted in FIG. 9, hooks 186 may be inserted into slots 105 to form an engagement between plate 102 and cables 182 and 184 during use. Alternatively, the engagement between the cables and the plate may be formed using, e.g., screws or other fasteners. A connecting mechanism 188 may be used to form an engagement between first cable 182 and second cable 184 during use. Connecting mechanism 188 may be attached to an end of first cable 182 opposite the end to which hook 186 is attached, as depicted in FIG. 8. Alternatively, connecting mechanism 188 may be separate from the cables.

Figure 10:
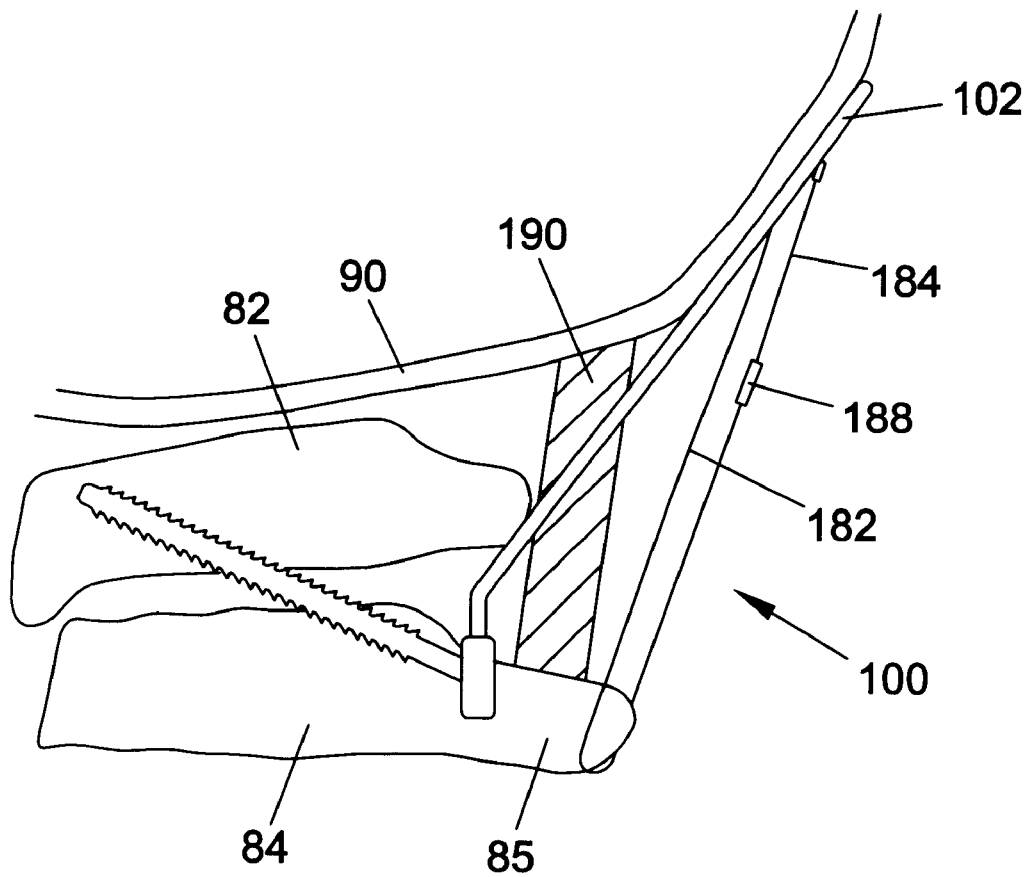
FIG. 10 depicts a cross-sectional side view of the fixation system of FIG. 8 in use.

FIG. 10 illustrates a spinal fixation system 100 including cables in use. Plate 102 may be attached to skull 90 as previously described with reference to FIG. 6c. A cable assembly may then be attached to plate 102 and to a portion of spine 80. In an embodiment depicted in FIG. 10, a portion of cable 182 is looped beneath spinous process 85 of vertebra 84. Cables 182 and 184 are then tensioned and connected to one another by connector 188 to maintain the cables in tension and to fuse vertebrae 84 and 82 and skull 90. Anchoring bolts 137 may then be inserted into vertebrae 84 and 82 and secured to arms 130 using connectors 150, as described previously.

In an embodiment, the spinal fixation system may further include optional bone graft material 190, as shown in FIG. 10. Bone graft material 190 may be inserted between occiput 90 and one or more vertebrae of spinal column 80 prior to attachment of the cable assembly. In the embodiment depicted in FIG. 10, bone graft material 190 is inserted between vertebra 84 and occiput 90. The cable assembly may be tensioned such that bone graft material 190 is compressed between vertebra 84 and occiput 90. Connecting mechanism 188 may be used to secure first cable 182 and second cable 184 such that movement of the cables with respect to one another is inhibited. As such, the cables may be held in tension such that compression of the bone graft material is maintained, thus facilitating fusion between spinal column 80 and occiput 90. It is to be understood that the embodiment depicted in FIG. 10 is exemplary only and that other configurations of the illustrated system are possible. For example, the cable assembly may include a single cable rather than the two cables depicted.

Figure 11:
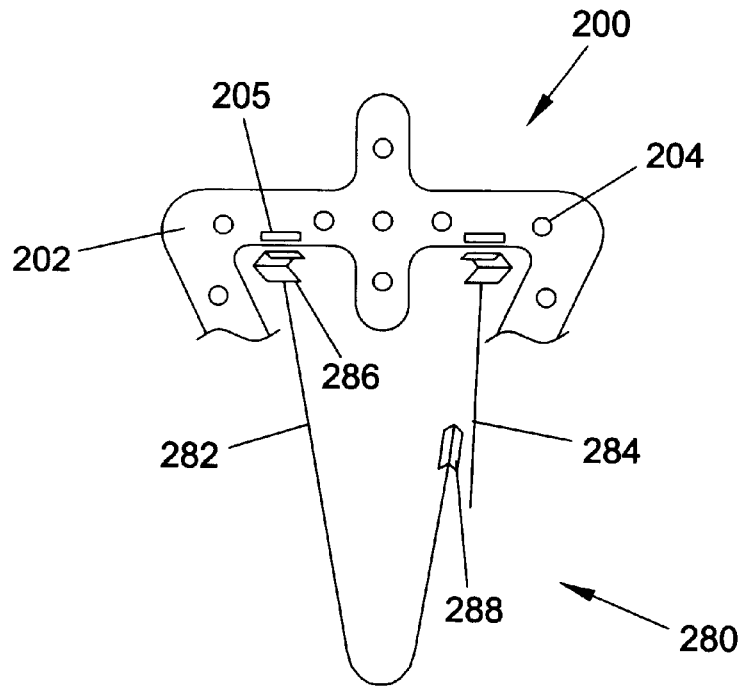
FIG. 11 depicts an alternate embodiment of an occipito-cervical spinal fixation system.

Turning now to FIG. 11, an alternate embodiment of an occipito-cervical spinal fixation system is depicted. Spinal fixation system 200 preferably includes a plate and a cable assembly. Fixation system 200 is preferably made from a biocompatible material such as titanium or stainless steel. As depicted in FIG. 11, plate 202 includes openings 204 formed therein through which the plate may be secured to a portion of a skull during use. Fixation system 200 may include a cable assembly 280 similar to cable assembly 180 (FIG. 8). Alternatively, cable assembly 280 may include a single cable. As depicted, plate 202 includes slots formed therein through which cable assembly 280 may be affixed to the plate during use. Hooks 286 may be inserted into slots 205 to form an engagement between plate 202 and cables 282 and 284. Cables 282 and 284 may include any substantially flexible material including, but not limited to, cloth, fiber, steel, nylon, monofilament, or various plastics. The cables are preferably made of a biocompatible material such as titanium or stainless steel. Connecting mechanism 288 may be used to form an engagement between first cable 282 and second cable 284. Connecting mechanism 288 may be affixed to an end of one of the cables; alternatively, coupling mechanism 288 may be separate from the cables. It is to be understood that the embodiment depicted in FIG. 11 is merely representative and that other configurations of the invention are possible. For example, the cable assembly may be secured to the plate using fasteners such as screws rather than hooks and slots.

Figure 12:
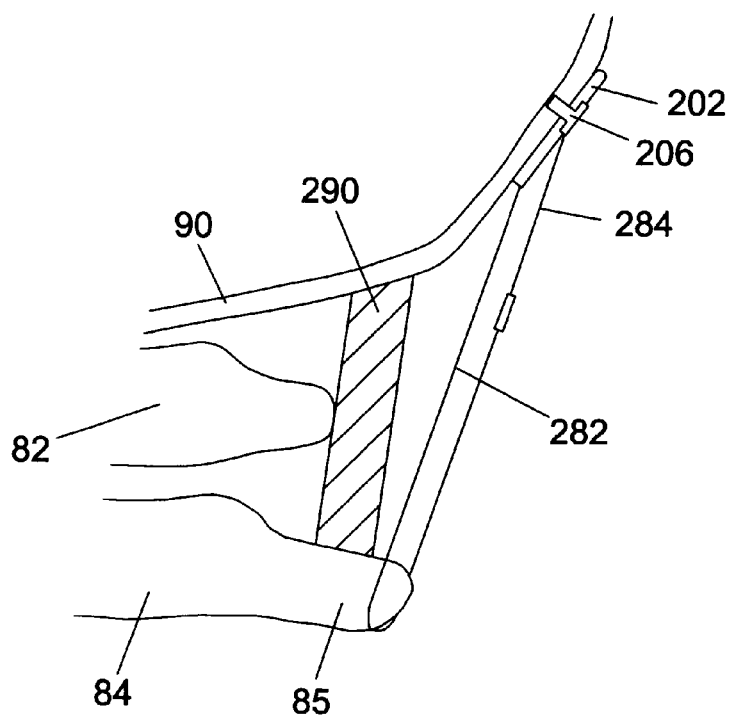
FIG. 12 depicts a cross-sectional side view of the fixation system of FIG. 11 in use.

As depicted in FIG. 12, plate 202 may be affixed to occiput 90 using connecting members 206. Connectors 206 may be similar to previously described connectors 106. A surgeon may form a plurality of holes in a portion of skull 90. Connectors 206 may then be inserted through the holes in the plate and the skull to secure the plate to the skull. Preferably, openings 204 and connecting members 206 are configured similarly to openings 104 and connecting members 106 as previously described such that upper surfaces of connecting members 206 are planar with an upper surface of plate 202 during; use. A cable assembly may then be attached to plate 202 and to a portion of spine 80. In an embodiment depicted in FIG. 12, a portion of cable 282 is looped beneath spinous process 85 of vertebra 84. Cables 282 and 284 are then tensioned and connected to one another by connector 288 to maintain the cables in tension and to fuse vertebrae 84 and 82 and skull 90.

In an embodiment, the spinal fixation system may further include optional bone graft material 290, as shown in FIG. 12. Bone graft material 290 may be inserted between occiput 90 and one or more vertebrae of spinal column 80 prior to attachment of the cable assembly. In the embodiment depicted in FIG. 12, bone graft material 190 is inserted between vertebra 84 and occiput 90. The cable assembly may be tensioned such that bone graft material 290 is compressed between vertebra 84 and occiput 90. Connecting mechanism 288 may be used to secure first cable 282 and second cable 284 such that movement of the cables with respect to one another is inhibited. As such, the cables may be held in tension such that compression of the bone graft material is maintained, thus facilitating fusion between spinal column 80 and occiput 90. It is to be understood that the embodiment depicted in FIG. 12 is exemplary only and that other configurations of the illustrated system are possible. For example, the cable assembly may include a single cable rather than the two cables depicted.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for mechanically fixating a region of a skull to a portion of a spine, comprising:
    a first portion of a plate configured to contact the region of the skull, wherein the first portion of the plate comprises openings configured to secure the first portion of the plate to the skull during use;
    a second portion of the plate extending from the first portion, wherein said second portion extends from the plate to an area that is adjacent to at least one vertebra;
    connecting members configured to engage the openings and secure the first portion of the plate to the region of the skull during use;
    a cable assembly configured to couple to an additional opening formed in the first portion; and
    an anchoring system for securing the second portion to cervical vertebrae,
    wherein the plate is a unitary structure wherein the first portion and the second portion are not releasably attached together.

2. The system of claim 1 wherein the second portion further comprises members configured to extend to opposite sides of the spine.

3. The system of claim 1 wherein the second portion comprises a proximal portion adjacent to first portion of the plate and a distal portion, wherein an angle between the proximal and distal portions is between approximately 100° to approximately 140°.

4. The system of claim 1 wherein the anchoring system comprises:
    anchoring bolts configured to be attached to the second portion, wherein the anchoring bolts engage at least one vertebra during use; and
    connectors for attaching the anchoring bolts to the second portion.

5. The system of claim 1 wherein the second portion comprises a proximal portion located adjacent to the first portion of the plate and a distal portion, and wherein the anchoring bolts are oriented at an angle between approximately 55° to approximately 75° with respect to the distal portion during use.

6. The system of claim 4 wherein at least one of the anchoring bolts comprises a bolt head, and wherein a surface of at least one of the connectors defines first radially oriented serrations, and wherein a surface of the bolt head defines second radially oriented serrations, and wherein the first serrations and the second serrations effect engagement between the at least one connector and the at least one anchoring bolt to inhibit rotation of the at least one anchoring bolt with respect to the at least one connector during use.

7. The system of claim 4 wherein the at least one connector comprises a first piece and a second piece, and wherein the second piece defines a hole, and wherein the first piece comprises a threaded projection, the threaded projection being configured to pass through the hole in the second piece during use.

8. The system of claim 7, wherein the at least one connector further comprises a locking nut, wherein during use, the threaded projection also passes through an opening in the bolt head and is secured by the locking nut.

9. The system of claim 1 wherein the cable assembly is configured to pass under a spinous process of a cervical vertebra during use.

10. The system of claim 1 wherein the cable assembly comprises:
   a first cable comprising a first end and a second end, and having a first hook affixed to a first end thereof;
   a second cable comprising a first end and a second end, and having a second hook affixed to a first end thereof; and
   a connecting mechanism configured to couple the first cable to the second cable during use;
   wherein the first hook is configured to engage the slot during use and wherein the second hook is configured to engage a second slot in the first portion during use.

11. The system of claim 1, further comprising bone graft material, wherein the bone graft material is inserted between the skull and a cervical vertebra during use.

12. The system of claim 1, wherein the connecting members are bone screws.

13. A system for mechanically fixating a region of a skull to a portion of a spine, comprising:
   a plate for contacting the region of the skull, wherein the plate comprises openings configured to accept connecting members that secure the plate to the skull during use;
   connecting members for securing the plate to the region of the skull; and
   a cable assembly for engaging a cervical vertebra of the spine, wherein the cable assembly is configured to be attached to the plate during use.

14. The system of claim 13 wherein the plate defines one or more slots, and wherein the cable assembly engages one or more slots during use.

15. The system of claim 13, further comprising bone graft material, wherein the bone graft material is inserted between a skull and a cervical vertebra during use.

16. The system of claim 13, wherein the cable assembly comprises two cables, and wherein a first end of each cable is configured to engage the plate during use, and further wherein a second end of a cable is configured to connect to another cable during use.

17. The system of claim 16, wherein one of the cables comprises a connecting mechanism for joining the two cables together.

18. The system of claim 1, wherein the anchoring system is configured to secure the second portion to cervical vertebrae C1 and C2.

19. A system for mechanically fixating a region of a skull to a portion of a spine, comprising:
   a plate configured to contact a region of a skull, wherein the plate comprises openings configured to secure the plate to the skull during use;
   arms extending from the plate, each arm extending from the plate to a position adjacent to at least one cervical vertebra of the spine;
   connecting members configured to engage the openings and secure the plate to the region of the skull during use;
   a cable assembly configured to be coupled to the plate; and
   an anchoring system for securing the arms to cervical vertebrae, wherein the anchoring system comprises anchoring bolts wherein each of the anchoring bolt are configured to be inserted into at least two cervical vertebrae.

20. The system of claim 19 wherein the at least one arm includes members configured to extend to opposite sides of the spine.

21. The system of claim 19 wherein the at least one arm comprises a portion proximate to the plate and a portion distal to the plate, and an angle between the proximate and distal portions, such that the distal portion is at an angle of from approximately 100° to approximately 140° with respect to the proximate portion during use.

22. The system of claim 21 wherein the anchoring bolts are oriented at an angle of from approximately 55° to approximately 75° with respect to the distal portions of the arms during use.

23. The system of claim 19 wherein the anchoring system comprises connectors for attaching the anchoring bolts to the arms.

24. The system of claim 23 wherein the anchoring bolts comprise a bolt head, and wherein a surface of the connectors defines first radially oriented serrations, and wherein a surface of the bolt heads defines second radially oriented serrations, and wherein the first serrations and the second serrations effect engagement between the connectors and the anchoring bolts to inhibit rotation of the anchoring bolts with respect to the connectors during use.

25. The system of claim 23 wherein at least one of the connectors comprises a first piece and a second piece, and wherein the second piece defines a hole, and wherein the first piece comprises a threaded projection, the threaded projection being configured to pass through the hole in the second piece during use.

26. The system of claim 25, wherein the at least one of the connectors further comprises a locking nut configured to secure the first piece to the second piece during use.

27. The system of claim 19 wherein the cable assembly is configured to pass under a spinous process of a cervical vertebra during use.

28. The system of claim 19 wherein the plate further comprises a slot, and wherein an end of the cable assembly engages the slot during use.

29. The system of claim 19 wherein the cable assembly comprises:
   a first cable comprising a hook coupled to a first end of the first cable;
   a second cable comprising a hook coupled to a first end of the second cable; and
   a cable connector configured to couple the first cable to the second cable during use;
   wherein the hook of the first cable and the hook of the second cable engage openings in the plate during use.

30. The system of claim 19, further comprising bone graft material configured to be inserted between the skull and an adjacent cervical vertebra during use.

31. The system of claim 19, wherein the connecting members are bone screws.

32. A system for mechanically fixating a region of a skull to a portion of a spine, comprising:
   a first portion of a plate configured to contact the region of the skull, wherein the first portion of the plate comprises openings configured to secure the first portion of the plate to the skull during use;
   a second portion of the plate extending from the first portion, wherein said second portion extends from the plate to an area that is adjacent to at least one vertebra;

connecting members configured to engage the openings and secure the first portion of the plate to the region of the skull during use;

connectors coupled to the second portion, wherein at least one connector comprises:
 a first piece having a projection;
 a second piece having an opening that is sized to allow the projection to pass through the opening;
 a locking nut configured to secure the first piece to the second piece and secure the connector to the second member; and
 a surface having radially oriented serrations;

anchoring bolts configured to be coupled to the connectors and to a vertebra, wherein at least one of the anchoring bolts comprises:
 a bolt head having an opening configured to allow the projection to pass through the bolt head; and
 a surface having radially oriented serrations that are configured to engage the serrations of the at least one connector to inhibit rotation of the anchoring bolt with respect to the at least one connector during use;

wherein the plate is a unitary structure wherein the first portion and the second portion are not releasably attached together.

33. The system of claim 32, further comprising a slot in the first portion, and a cable assembly having an end, wherein the end is configured to engage the slot to couple the cable assembly to the first portion.

34. The system of claim 32, further comprising a first cable, a second cable, and a connecting mechanism, wherein an end of the first cable couples to a slot in the first portion, wherein an end of the second cable couples to a second slot in the first portion, and wherein the connecting mechanism couples the first cable to the second cable during use.

* * * * *

UNITED STATES PATENT AND TRADEMARK OFFICE
CERTIFICATE OF CORRECTION

PATENT NO.    : 6,146,382
DATED         : November 14, 2000
INVENTOR(S)   : R. John Hurlbert It is certified that error appears in the above-identified patent and that said Letters Patent is hereby corrected as shown below:

Claim 19, column 12,
Line 1, after "of the anchoring", please delete "bolt" and insert -- bolts --.

Signed and Sealed this

Twenty-third Day of October, 2001

*Attest:*

*Attesting Officer*

NICHOLAS P. GODICI
*Acting Director of the United States Patent and Trademark Office*